(12) United States Patent
Mischler et al.

(10) Patent No.: US 6,531,702 B1
(45) Date of Patent: Mar. 11, 2003

(54) SAMPLE CARRIER FOR THE IR SPECTROSCOPY OF SAMPLE LIQUIDS

(75) Inventors: Reinhold Mischler, Ludwigshafen (DE); Dirk Boecker, Palo Alto, CA (US)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/579,001

(22) Filed: May 25, 2000

(30) Foreign Application Priority Data

May 27, 1999 (DE) .......................... 199 19 608

(51) Int. Cl.$^7$ ............................................. G01N 21/01
(52) U.S. Cl. .................................. 250/339.12
(58) Field of Search .............. 250/339.11, 339.12; 356/244, 246; 422/73

(56) References Cited

U.S. PATENT DOCUMENTS

| | | | |
|---|---|---|---|
| 4,088,448 A | 5/1978 | Lilja et al. | 422/102 |
| 4,323,536 A | 4/1982 | Columbus | 422/56 |
| 4,596,695 A | 6/1986 | Cottingham | 422/58 |
| 4,756,884 A * | 7/1988 | Hillman et al. | 422/73 |
| 4,775,515 A | 10/1988 | Cottingham | 422/73 |
| 4,882,493 A | 11/1989 | Lodder et al. | 250/353 |
| 4,900,663 A | 2/1990 | Wie et al. | 435/7.32 |
| 4,904,449 A | 2/1990 | Heckmann | 422/87 |
| 5,164,598 A | 11/1992 | Hillman et al. | 250/341 |
| 5,171,995 A | 12/1992 | Gast et al. | 250/339.08 |
| 5,470,757 A | 11/1995 | Gagnon et al. | |
| 5,519,218 A | 5/1996 | Chang | 250/339.07 |
| 5,605,838 A * | 2/1997 | Backhaus et al. | 436/34 |
| 5,658,413 A * | 8/1997 | Kaltenbach et al. | 156/272.8 |
| 5,882,465 A | 3/1999 | McReynolds | 156/285 |
| 5,977,545 A | 11/1999 | Haar et al. | |

FOREIGN PATENT DOCUMENTS

| | | |
|---|---|---|
| DE | 3606124 A1 | 3/1987 |
| DE | 3739046 A1 | 5/1988 |
| DE | 4030699 C1 | 10/1991 |
| DE | 692 26 528 T2 | 1/1993 |
| DE | 195 20 446 A1 | 12/1996 |
| EP | 0014797 A1 | 9/1980 |
| EP | 0107631 A2 | 5/1984 |
| EP | 0282901 A2 | 9/1988 |
| GB | 2231150 A | 11/1990 |
| GB | 2332945 A | 7/1999 |
| WO | WO 81/03224 | 11/1981 |
| WO | WO93/00580 | 1/1993 |
| WO | WO 96/07885 | 3/1996 |

OTHER PUBLICATIONS

JP 60–56261 A., In: Patents Abstracts of Japan, P–377, Aug. 2, 1985, vol. 9, No. 18; ganzes Abstract.

* cited by examiner

*Primary Examiner*—Constantine Hannaher
*Assistant Examiner*—Shun Lee
(74) *Attorney, Agent, or Firm*—Barnes & Thornburg

(57) ABSTRACT

Sample carrier for IR spectroscopy which has a sample application zone as well as at least one groove-shaped channel into which liquid is drawn from the sample application zone as a result of capillary forces. A method for IR spectroscopy using a sample carrier according to the invention and a system for IR spectroscopy using the sample carrier according to the invention.

17 Claims, 2 Drawing Sheets

SAMPLE CARRIER FOR THE IR SPECTROSCOPY OF SAMPLE LIQUIDS

TECHNICAL FIELD OF THE DISCLOSURE

The present invention concerns a sample carrier for IR spectroscopy which has a sample application zone as well as at least one groove-shaped channel into which liquid is drawn from the sample application zone as a result of capillary forces. The present invention also concerns a method for IR spectroscopy using a sample carrier according to the invention and a system for IR spectroscopy using the sample carrier according to the invention.

BACKGROUND OF THE DISCLOSURE

Sample carriers for carrying out IR spectroscopy are already known in the prior art in which sample liquid is placed in a depression and an IR-spectroscopic analysis is carried out after the sample liquid has dried. A disadvantage of such sample carriers is that the mostly small sample volumes have to be dosed precisely for a quantitative analysis. In addition the effect occurs with sample carriers with depressions that liquids containing protein form a drying ring in which a relatively high amount of sample is present in the ring region whereas only very small amounts of sample are present inside the ring. This or other drying patterns can make it difficult or even impossible to qualitatively and quantitatively analyse the sample liquid by means of IR spectroscopy.

Other sample carriers for IR spectroscopy are also known in the prior art which are in the form of nets onto which the sample liquid is applied such that the liquid spreads out in the meshes of the net. The nets already enable a dosing of the sample liquid in such a manner that a specific sample volume is imbibed per mesh with a known viscosity of the sample. However, a disadvantage of such sample carriers is that their manufacture and handling can be complicated.

SUMMARY OF THE DISCLOSURE

The object of the present invention was to propose sample carriers which are easy to manufacture, enable a simple handling and achieve a relatively uniform and predetermined distribution of the sample. Sample carriers according to the invention can also advantageously provide dosing of the sample liquid in such a manner that a certain amount of the sample liquid is recovered on a certain area of the sample carrier.

Sample carriers for IR spectroscopy according to the invention have a sample application zone and at least one groove-shaped channel into which liquid is drawn from the sample application zone as a result of capillary forces. In a method according to the invention for the IR spectroscopy of a sample liquid, a sample carrier according to the invention is firstly provided, the sample liquid is applied to the application zone of the sample carrier and the zone of the sample carrier in which the at least one groove-shaped channel is located (spreading zone) is irradiated with IR radiation. Subsequently the radiation which is reflected from the spreading zone or transmitted through the spreading zone is detected and evaluated in order to carry out a qualitative and/or quantitative analysis of the sample liquid.

The invention additionally comprises a system for carrying out IR spectroscopy of a sample liquid with the following elements:

A sample carrier with an application zone for the application of a liquid sample and a spreading zone connected to the application zone which has at least one groove-shaped channel into which liquid is drawn from the sample application zone as a result of capillary forces, a source of IR radiation to irradiate at least a part of the spreading zone of the sample carrier, a detector to detect the radiation that is reflected from the spreading zone or transmitted through the spreading zone, an evaluation unit to evaluate the detector signals for the qualitative and/or quantitative analysis of the sample liquid.

DETAILED DESCRIPTION OF THE DISCLOSURE

Figure 1:
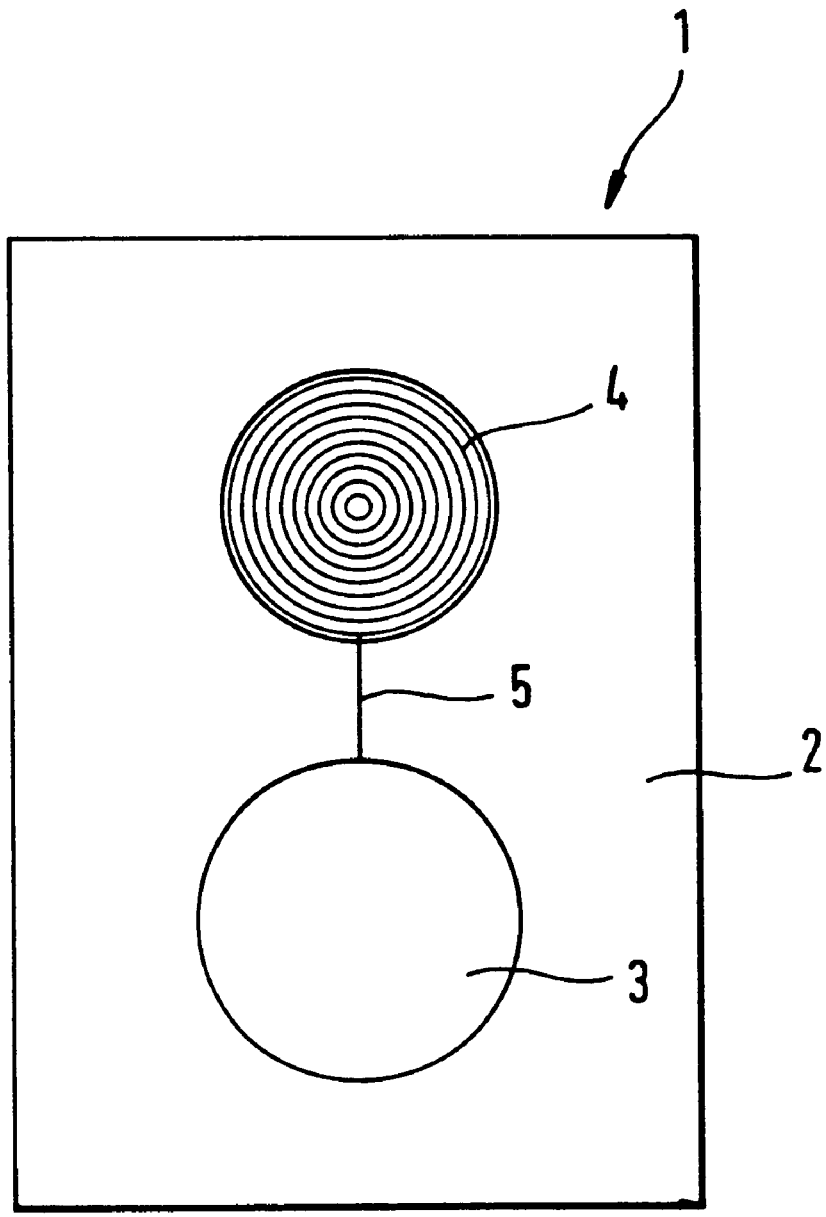
FIG. 1 is a top elevational view of a sample carrier described herein.

Sample carriers according to the invention have an application zone for the application of a liquid sample as well as a spreading zone. These two units are both arranged on the sample carrier and at least the spreading zone, but preferably the spreading zone and also the application zone, are accessible from the upper side of the carrier. If it is intended to use the sample carrier to carry out IR spectroscopy by means of reflection spectroscopy, a material can be selected which is essentially impermeable to IR radiation. For use in reflection spectroscopy the sample carrier is preferably provided with a surface coating which reflects IR radiation without essentially absorbing it or at least not specifically absorbing it. As a result the material of the sample carrier does not contribute to the reflection signal or at least there are no absorption bands caused by the sample carrier. A surface coating of the carrier can for example be achieved by vapour-depositing gold or aluminum on the carrier.

If in contrast the sample carrier is to be used for transmission spectroscopy, materials are used which do not or only negligibly absorb infrared radiation. Suitable materials are for example silicon, germanium, quartz glass and alkali halogenides. Semiconductor materials such as silicon and germanium are particularly advantageous since they can be produced with a high purity and methods for treating their surface are well-known from semiconductor electronics. Plastics which are sufficiently permeable to the radiation in the IR range that is used also come into consideration as a material for the sample carrier. In particular it has turned out that polyethylene is adequately permeable in some ranges.

The sample application zone of sample carriers according to the invention is preferably a depression or a chamber into which sample liquid can be added. The sample application zone can also be simply a region on the sample carrier which adjoins the spreading zone. The sample application zone can also be an opening of the carrier such as a capillary gap which draws in the applied sample. In the latter case the sample application zone hardly needs a holding capacity since the sample liquid can be directly passed into the groove-shaped channel. However, in the case of the preferred embodiments of a sample application zone in the form of a depression or chamber, the holding capacity is preferably larger than the holding capacity of the groove-shaped channel. This ensures that the amount of liquid needed to fill up the groove-shaped channel can be firstly completely deposited in the sample application zone before it is drawn into the groove-shaped channel by capillary forces. The holding capacity of the sample application zone is preferably between 0.3 and 5 μl, particularly preferably between 0.1 and 1.5 μl. The sample application zone either leads directly into the groove-shaped channel or is connected to the groove-shaped channel by a fluid channel. The sample application zone is preferably designed such that the groove-shaped channel is filled when the sample is applied without additional measures and without particularly high demands on the positioning of the sample application. For example the sample application zone can be in the shape of a well which tapers towards the bottom into the lower region of which a channel leads which in turn is connected to the groove-shaped channel. However, since such a sample carrier is more complicated to manufacture due to the channel, sample carriers are preferred in which a sample application zone and groove-shaped channel and optionally a connecting channel can be manufactured without having to take account of undercuts and closed channels. A sample carrier which is technically easier to manufacture has a sample application zone in the shape of a well which is directly connected to the groove-shaped channel i.e. this groove-shaped channel leads into the bottom of the sample application zone. The holding capacity of the sample application zone should be such that the bottom surface of the sample application zone is completely filled when a particular volume is applied so that it can be ensured that sample liquid reaches the area where the groove-shaped channel joins. In addition to the holding capacity of the sample application zone, the type of sample (viscosity, surface tension) and the properties of the surface of the sample application zone are important. It is preferred that the sample application zone has a surface tension of more than 80 mN/m so that the sample liquid can spread well and it can thus be ensured that it reaches the area where the groove-shaped channel joins. Alternatively the sample application zone can also be filled with a material which causes spreading in order to again ensure that sample liquid can reach the area from which it is drawn into the diagnostic test carrier as a result of capillary forces. Suitable materials are for example fleeces ar absorbent inorganic layers such as kieselguhr and aluminum oxide etc.

In the present patent application the region of the sample carrier which is used de facto for analysis by IR radiation is referred to as the analytical region. In contrast the spreading zone is the region of the sample carrier in which the at least one groove-shaped channel is located. The analytical region can be larger as well as smaller than the spreading zone when the sample carrier is used according to the invention.

Figure 2:
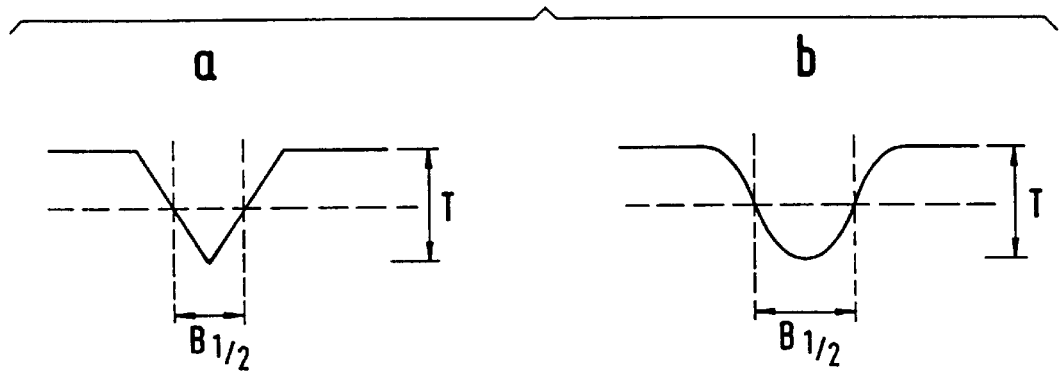
FIG. 2 panel (a) shows a cross sectional view of a V-shaped channel which can be defined in the sample carrier of FIG. 1, while panel (b) shows a cross sectional view of a sinus-shaped channel which can be defined in the sample carrier of FIG. 1.
Figure 3:
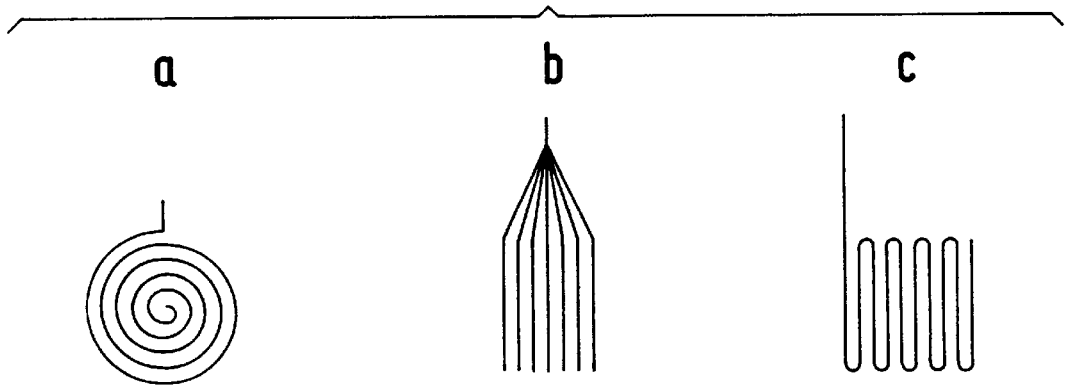
FIG. 3 panels (a), (b), and (c) depict exemplary surface arrangements of groove-shaped channels which can be defined in the sample carrier of FIG. 1.

An important aspect of the present invention is the groove-shaped channel which is designed such that it takes up liquid by capillary forces. According to the invention a groove-shaped channel is open at the top such that liquid which has spread within the channel dries up. The groove of the groove-shaped channel can for example have a V-shaped profile or a sinus-shaped profile. The depth of the groove is typically in the range from 10 μm to 200 μm. The so-called half width is also important for the function of the groove-shaped channel. A V-shaped and a sinus-shaped channel are shown in cross-section in FIGS. 2A and 2B. The half width ($B_{1/2}$) is the width of the channel at the point where the channel has half of its total depth (T). Preferred half widths within the scope of the invention are in the range from 10 to 200 μm. A good capillary effect is usually achieved with groove widths below 100 μm. In order to adequately disperse the sample over an adequately large area, the groove-shaped channel preferably has a length of more than 5 cm and the groove is designed such that the said length is filled with sample liquid provided adequate sample liquid has been applied. A further aspect is the density of sample liquid in a particular area which is achieved by the groove-shaped channel. It is important for an application of the sample carrier according to the invention for IR spectroscopy that an adequate amount of sample can be brought into the analytical region of the IR spectrometer by means of the groove-shaped channel. As a result of usually rotationally symmetrical optics, the cone of radiation of IR spectrometers is usually circular and consequently inventive sample carriers are preferred in which the groove-shaped channel in the surface is arranged such that a high surface density is achieved in a circular region. This can be achieved in particular with a groove-shaped channel which is in the shape of a helix or spiral. However, arrangements are also possible within the scope of the invention in which the groove-shaped channel is arranged in a meander shape. Finally another design is to have groove-shaped channels which branch out from the sample application zone or from a channel which is connected to the sample application zone which run parallel to one another in the analytical region and thus provide a high surface density of sample in this region. In the said embodiments an analytical region of less than 3 $cm^2$ is preferably formed which results from a close arrangement of groove-shaped channels. Examples of surface arrangements of the groove-shaped channel are shown in FIG. 3.

Hydrophilic materials or hydrophilically-coated materials with a surface tension of preferably less than 80 mN/m can be preferably used for the region of the groove-shaped channel.

The sample carrier according to the invention can for example be manufactured by one of the following processes:

A block or plate of sample carrier material is prepared and channels for the groove-shaped channel and a well for the sample application zone are milled using a high-speed machine. In addition the structure of the sample application zone and groove-shaped channel can be stamped into a plate or such like. This is possible especially for thicker aluminum foils or other metal foils. The sample carrier can also be manufactured in an injection moulding process. Finally it is also possible to etch the channels or grooves into the sample carrier as is for example well-known for silicon and germanium in the prior art.

The structure and function of a sample carrier according to the invention are illustrated in more detail by FIG. 1:

The sample carrier (1) has a holder (2) on which a sample application zone (3) and a groove-shaped channel (4) are disposed which are connected together via a channel (5). The sample carrier is manufactured from the plastic polymethylmethacrylate. The area of the groove-shaped channel (4) was subsequently vapour-coated with aluminum. The depressions of the sample carrier, the sample application zone, channel (5) and groove-shaped channels do not have any undercuts. The sample application zone has a diameter of 0.5 cm and a depth of 1 mm. The channel has a depth of 0.1 mm and a width of 100 μm. The analytical region which is formed by the spirally coiled, groove-shaped channel (4) has a diameter of 0.3 cm. The sample carrier that is shown is designed for the analysis of whole blood. A groove-shaped channel with a depth of 0.4 mm and a half width of 0.2 mm was selected for this sample material. The length of the groove-shaped channel that is shown is ca. 5 cm.

Figure 4:
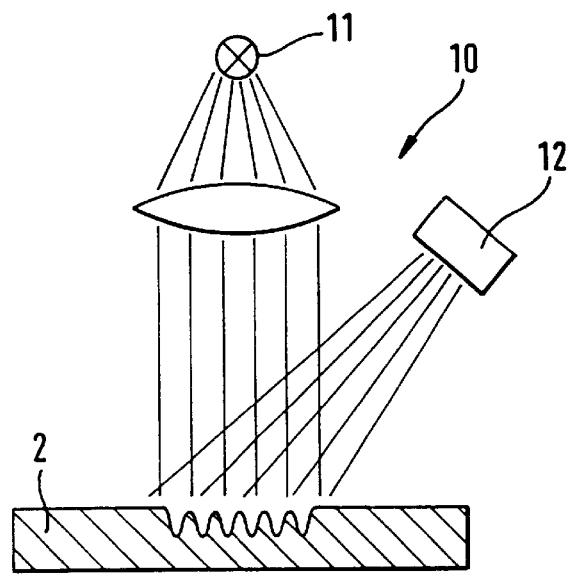
FIG. 4 is a schematic representation of an IR spectroscopy system utilizing a sample carrier described herein.

FIG. 4 shows a system for IR spectroscopy using a carrier according to the invention. Infrared spectroscopy with sample carriers on which a liquid sample is dried on before the analysis are known in the prior art. Special reference is made to the U.S. Pat. No. 5,605,838 in relation to the present invention. FIG. 4 shows a system (10) with a source of IR radiation (11) which is used to irradiate the analytical region of a sample carrier (2) according to the invention in which the groove-shaped channels are disposed. Radiation reflected from the sample carrier is detected with the detector (12) and can be evaluated with an evaluation device. The system according to the invention can be used to record the IR spectrum of a sample or to enable the quantitative determination of one or several analytes.

In a method for the IR spectroscopy of a sample liquid a sample is firstly placed on the sample application zone of the sample carrier which is then drawn into the groove-shaped channel of the sample carrier by means of capillary forces. The sample which is present in the groove-shaped channel is now substantially dried which can be facilitated by applying a vacuum or storing the carrier in a dry atmosphere. However, it is usually sufficient to store the carrier for several minutes in a normal atmosphere to achieve an adequate drying. As described in U.S. Pat. No. 5,605,838 a drying process is preferred in which the solvent content of the sample which is usually the water component is not completely removed but is reduced to below 20% by weight. After drying or also to facilitate the drying, the analytical zone of the carrier is irradiated with IR radiation and the radiation reflected from the analytical zone or transmitted through the analytical zone is detected with a detector. Suitable sources of radiation and detectors for analysing IR spectra are well known in the prior art.

What is claimed is:

1. Sample carrier for IR spectroscopy comprising a sample application zone and at least one groove-shaped channel into which liquid is drawn from the sample application zone as a result of capillary forces.

2. Sample carrier as claimed in claim 1, in which the at least one groove-shaped channel is arranged in a spiral shape.

3. Sample carrier as claimed in claim 1, in which the groove-shaped channel is arranged in a meander shape.

4. Sample carrier as claimed in claim 1, wherein the sample carrier has a plurality of groove-shaped channels arranged next to one another.

5. Sample carrier as claimed in claim 1, in which the at least one groove-shaped channel has a V-shaped profile in cross-section.

6. Sample carrier as claimed in claim 1, in which the at least one groove-shaped channel has a sinus-shaped profile in cross-section.

7. Sample carrier as claimed in claim 1, in which the width of the groove-shaped channel is less than 100 μm.

8. Sample carrier as claimed in claim 1, in which the ratio of the width to depth of the groove-shaped channel is 0.5 to 2.0.

9. Sample carrier as claimed in claim 1, in which the half width of the groove-shaped channel is 0.1 to 1.0 mm.

10. Sample carrier as claimed in claim 1, in which the length of the groove-shaped channel is more than 5 cm.

11. Sample carrier as claimed in claim 1, wherein (i) the groove-shaped channel defines an analytical region and (ii) the analytical region has an area that is less than 3 cm$^2$.

12. Sample carrier as claimed in claim 1, wherein (i) the groove-shaped channel defines an analytical region and (ii) the groove-shaped channel defining the analytical region has a length greater than 1 cm.

13. Sample carrier as claimed in claim 1, in which at least the region in which the at least one groove-shaped channel is located is coated with aluminum or gold.

14. Sample carrier as claimed in claim 1, which is manufactured from a plastic by a moulding process.

15. System for carrying out IR spectroscopy of a sample liquid with a sample carrier comprising:

a sample carrier which has a sample application zone and at least one groove-shaped channel into which liquid is drawn from the sample application zone as a result of capillary forces, a source of IR radiation to irradiate the sample carrier in the region in which the groove-shaped channel is located, a detector to detect the radiation that is reflected from the sample carrier or to detect radiation transmitted through the sample carrier, an evaluation unit to evaluate the detected radiation for the qualitative and/or quantitative analysis of the sample liquid.

16. Method for the IR spectroscopy of a sample liquid comprising the steps providing a sample carrier with an application zone for applying a liquid sample and with at least one groove-shaped channel that is connected to the application zone into which liquid is drawn from the sample application zone as a result of capillary forces, applying sample liquid to the application zone, irradiating the region of the sample carrier in which the at least one groove-shaped channel is located with IR radiation, detecting radiation that is reflected from the sample carrier or transmitted through the sample carrier, evaluation of the detected radiation for the qualitative and/or quantitative analysis of the sample liquid.

17. Method as claimed in claim 16, in which the sample liquid is located in the groove-shaped channel is dried before the evaluation.

* * * * *